United States Patent [19]

Jakob et al.

[11] Patent Number: 5,191,085
[45] Date of Patent: Mar. 2, 1993

[54] OPTICALLY ACTIVE SALTS OF A SUBSTITUTED THIAZOLIDINE-4-CARBOXYLATE AND 3-CYANO-HYDROXYPROPYL TRIMETHYL-AMMONIUM, THEIR PRODUCTION AND USES

[75] Inventors: Harald Jakob, Hasselroth; Klaus Huthmacher, Gelnhausen; Herbert Klenk, Hanau, all of Fed. Rep. of Germany

[73] Assignee: Degussa Aktiengesellschaft, Frankfurt am Main, Fed. Rep. of Germany

[21] Appl. No.: 675,623

[22] Filed: Mar. 27, 1991

[30] Foreign Application Priority Data

May 15, 1990 [DE] Fed. Rep. of Germany ....... 4015573

[51] Int. Cl.⁵ .......................................... C07D 277/06
[52] U.S. Cl. .................... 548/201; 548/147; 548/188
[58] Field of Search ............ 548/201, 147, 188; 558/354

[56] References Cited

U.S. PATENT DOCUMENTS

| 4,656,303 | 4/1987 | Kurono | 558/345 |
| 4,914,208 | 4/1990 | Jakob | 548/201 |

FOREIGN PATENT DOCUMENTS

| 157315 | 4/1984 | European Pat. Off. |
| 0312726 | 4/1989 | European Pat. Off. |
| 1907035 | 10/1984 | Fed. Rep. of Germany |
| 2536391 | 5/1984 | France | 558/354 |

OTHER PUBLICATIONS

Hoppe-Seylers Zeitschrift f. physiol. Chemie 318, (1960) pp. 129-137 (In German).

*Primary Examiner*—Robert Gerstl
*Attorney, Agent, or Firm*—Beveridge, DeGrandi, Weilacher & Young

[57] ABSTRACT

Optically active salts are disclosed of the formula (I):

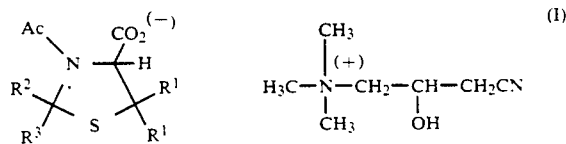

wherein Ac represents an acyl group, $R^1$ hydrogen or methyl, $R^2$ and $R^3$ identical or different substitutes, preferably methyl. The salts can be obtained from the corresponding optically active carbonic acid and DL-3-cyano-2-hydroxypropyl trimethylammonium hydroxide. The diastereomeric salt pairs are easily split from one another and separated again, so that the process is suited for producing optically active 3-cyano-2-hydroxypropyl trimethylammonium salts.

7 Claims, No Drawings

OPTICALLY ACTIVE SALTS OF A SUBSTITUTED THIAZOLIDINE-4-CARBOXYLATE AND 3-CYANO-HYDROXYPROPYL TRIMETHYL-AMMONIUM, THEIR PRODUCTION AND USES

BACKGROUND OF THE INVENTION

The present invention relates to new optically active salts obtained from a substituted thiazolidine-4-carboxylate and 3-cyano-2-hydroxypropyl trimethylammonium, their production and uses thereof. A preferred aspect of the invention relates to obtaining of L-(−)-3-cyano-2-hydroxypropyl trimethylammonium chloride (L-carnitine nitrile chloride), a valuable constituent for the synthesis of L-carnitine.

L-carnitine, also known as vitamin $B_T$, is increasingly being used in dietetic and pharmaceutical preparations for the treatment of injured myocardia, chronic circulatory disturbances, as well as for increasing functional capacity. Most chemical processes for the production of L-carnitine involve racemate resolution of a carnitine precursor. A racemate resolution of the precursor D,L-carnitine amide by using an optically active acid is known (East German Patent DD-PS 23217, German Published Patent Applications DE-OS 29 27 672, DE-OS 33 42 713). It is especially disadvantageous that D,L-carnitine amide must first specifically be produced from D,L-carnitine nitrile chloride. Compared to a racemate resolution at the D,L-carnitine nitrile chloride stage, which can be directly saponified to carnitine, an additional reaction stage is required.

Common features of a racemate resolution of D,L-carnitine nitrile chloride, the production of which generally is performed by the cyaniding of D,L-3-chloro-2-hydroxypropyl trimethylammoniumchloride or D,L-epoxypropyl trimethylammoniumchloride, are the conversion of the chloride into the hydroxide, reaction with an optically active acid, separation of the diastereomeric salts and the separation of the same with a strong acid. As a result, the optically active carnitine nitrile salt is obtained and the introduced optically active acid is recovered.

As an optically active acid for the racemate resolution of carnitine nitrile chloride there were proposed, for example, D-tartaric acid and D-camphor-10-sulfonic acid. However, minor differences in solubility made frequent recrystallization of the diastereomeric salts necessary. The combined use of D-camphor-10-sulfonic acid and dibenzoyl-L-tartaric acid (E. Strack et al., Z. physiol. Chem 318, 129 (1960)) provided an improvement. However, the use of two resolution agents results in high costs and make the process unsuitable for industrial application. With exclusive use of dibenzoyl-L-tartaric acid, the difference in solubility for both diastereomers is small, which again affects the yield.

The use of optically active N-acetyl-glutamic acid as resolution acid (Japanese Patent JP-B 43-8248, Dutch Patent NL-A 6614321) has also become known. In order to obtain the L-carnitine nitrile salt, there is required not the naturally occurring N-acetyl-L-glutaminic acid, but its antipode N-acetyl-D-glutaminic acid. The latter is not independently present in sufficient quantity, however, and must be produced by using D-carnitine nitrile chloride. However, if the slightly soluble salt of D-carnitine nitrile and N-acetyl-L-glutaminic acid is first separated from the diastereomeric pair, obtaining an optically pure L-carnitine-N-acetyl-D-glutamate from the mother liquor requires a multiple fractionating crystallization.

In order to improve the efficiency of the above-mentioned resolution reagents and to increase the optical purity of the desired carnitine nitrile salt, it was suggested to subsequently add an additional fractionating crystallization of a salt from the initially obtained optically active carnitine nitrile hydroxide and an optically inactive acid, such as oxal acid or perchloro acid (JP-A 62-286959). The entire process effort was, however, increased significantly. The racemate resolution using exclusively fractionating crystallization of D,L-carnitine nitrile oxalate or perchlorate only provides small chemical and optical yields (French Patent Applications FR-A 2 529 545, FR-A 2 536 391).

Processes for racemate resolution of D,L-3-chloro-2-hydroxypropyl trimethylammonium chloride, i.e., the precursor to D,L-3-cyano-2-hydroxypropyl trimethylammonium chloride, have also become known. According to European Patent Application EP-A 312 726, tartaric acid was used as the separation reagent. The tartaric acid, however, leaves much to be desired as a resolution reagent for technological purposes, because of its water solubility. Thus, it can only be recovered with much difficulty from the aqueous solutions that are obtained during the release of the L- or D,L-3-chloro-2-hydroxypropyl trimethylammonium chloride from the diastereomeric salt. Furthermore, the yield is not satisfactory due to irreversible side reactions, among other things.

Optical salts from a substituted thiazolidine-4-carboxylate and 3-chloro-2-hydroxypropyl trimethylammonium are known from European Patent Application EP-A 312 726. These salts are produced from a substituted optically active thiazolidine-4-carbonic acid that is first converted to the trimethylammonium salt by means of trimethylamine and subsequently is reacted with epichlorohydrin. The resulting diastereomeric salt pairs exhibit pronounced different solubilities, so that they can be separated through fractionation crystallization. By means of acid separation of the salt pair, L-(−)-3-chloro-2-hydroxy trimethylammonium chloride can be obtained, which can be converted to the 3-cyano compound and by way of hydrolysis to L-(−)-carnitine.

Although this method has the advantage that during the reaction, apart from the desired L-(−)-3-chloro-2-hydroxypropyl ammonium chloride, the produced undesirable D-enantiomerics as well as the racemic form can be utilized for cationization purposes, in practice, this entails some drawbacks. Thus, the reaction with trimethylamine and epichlorohydrin requires an extraordinarily high degree of technological efforts due to annoying odors in connection therewith and the high toxicity. Also, traces of non-reacted starting materials must be separated from the system and disposed of in a safe manner. The effort needed for the technological measures, e.g., steam distillation, including necessary safety measures for the contact with epichlorohydrin and the like, quickly exceed the utility of being able to utilize the D-enantiomers.

An object of the present invention is to eliminate the drawbacks of the known methods for producing the optically active 3-cyano-2-hydroxy trimethylammonium chloride necessary for the carnitine synthesis.

A further object is to provide optically active salts that can be produced in a simple and economical manner and that are suitable for racemate resolution of the cation of the salts, i.e., the D,L-3-cyano-2-hydroxytrimethylammonium, practically without any loss of the optically active anion of these salts.

SUMMARY OF THE INVENTION

In achieving the above as well as other objects, one feature of the present invention resides in optically active salts of the formula (I):

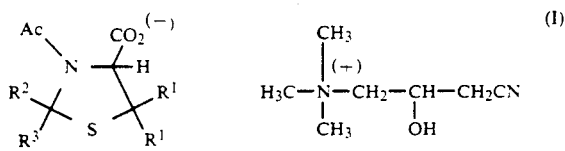

where:
- $R^1$ represents hydrogen or methyl;
- $R^2$ and $R^3$, which may be identical or different, represent hydrogen, alkyl with 1 to 8 C atoms, alkenyl with 2 to 8 C atoms, $C_5$ or $C_6$ cycloalkyl, or aryl, or $R^2$ and $R^3$ taken together are alkylene with 4 to 11 C atoms;
- and Ac represents an acyl group.

Especially preferred salts are those from D-(+)-3-formyl-2,2,5,5-tetramethyl thiazolidine-4-carboxylate and L-(−)-3-cyano-2-hydroxypropyl trimethylammonium as well as from L-(−)-3-formyl-2,2,5,5-tetramethyl thiazolidine-4-carboxylate and D-(+)-3-cyano-2-hydroxypropyl trimethylammonium.

$R^2$ and $R^3$ are preferably identical and represent methyl or ethyl, or $R^2$ and $R^3$ taken together form pentamethylene. With respect to the acyl group, there can be mentioned, e.g., benzoyl, tosyl, nitrophenyl sulfonyl, acetyl, or formyl.

The optically active salts according to the present invention of formula (I) are produced by reacting D,L-3-cyano-2-hydroxypropyl trimethylammonium hydroxide with an optically active acid of the formula (II):

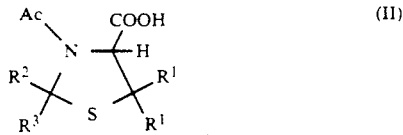

where $R^1$, $R^2$, $R^3$ and Ac have the meaning as in formula (I), above. If desired, the resulting diastereomeric salt pairs are separated from one another through fractionating crystallization.

The enantiomerically pure thiazolidine-4-carbonic acid of formula (II) can be obtained in a known manner (see Belgian Patent BE-PS 738 520) from an optically active β-mercapto-α-amino acid and an aldehyde or ketone with subsequent acylation. As an optically active acid there may be used, for example, L-cysteine ($R^1$=H) or D- or L-2-amino-3-methyl-3-mercaptobutyric acid (see British Patent GB-PS 585 413, German Published Patent Application 21 38 121).

DETAILED DESCRIPTION OF INVENTION

With the process of the present invention, initially D,L-carnitine nitrile chloride or the D,L-carnitine nitrile salt of another optically inactive acid is converted to D,L-carnitine nitrile hydroxide in a known manner. For this purpose particularly, anion exchangers or electrodialysis are suitable. The formed D,L-carnitine nitrile hydroxide is reacted with an equivalent amount of an optically active acid of formula (II), whereby the diastereomeric salts of formula (I) form from the optically active carboxylate-counterion and the D,L-carnitine nitrile cation.

The reaction is preferably performed in the presence of a protic solvent, especially water. Especially preferred is the racemic carnitine nitrile hydroxide introduced in aqueous phase and mixed with the thiazolidine-4-carbonic acid until reaching the neutral point. After removal of the water, the diastereomeric salt pair mixture can be separated into both salt pairs by means of fractionating crystallization of an organic solvent.

A special advantage of the process according to the present invention resides in the fact that the salts of the appropriate diastereomeric salt pairs in organic solvents exhibit considerable differences as to solubility, thus allowing for easy separation in crystallizate and mother liquor. In general, the salts of the D-acids (II) are less or even significantly less soluble with the L-(−)-carnitine nitrile compared to the diastereomeric DD-salts. Of course, the same applies for the relationship between the LD-salts and the LL-salts, so that an isolation of the LL-salts with high optical purity from the mother liquor is possible.

As solvents for the fractionating crystallization of the diastereomeric salt pairs there can be used ($C_1$–$C_6$)-alcohols, particularly ($C_1$–$C_4$)-alcohols; ($C_3$–$C_7$)-ketones, such as particularly acetone and methylisobutylketone (MIBK); cyclical ethers, such as, for example, tetrahydrofuran and dioxane; alkene glycol ethers with 3 to 7 C atoms, particularly ethylene glycol monomethyl ether, or mixtures of such solvents. Preferred solvent mixtures are n-butanol/acetone, i-butanol/acetone, methylisobutylketone/acetone, n-butanol/tetrahydrofuran or MIBK/tetrahydrofuran mixtures.

The fractionating crystallization preferably takes place in anhydrous solvents. After the salt formation, water which is normally present is distilled off. The concomitant use of solvents forming azeotropes with water, especially such as are used for the crystallization, is advantageous. The less soluble salt pair crystallizes from the organic solution during cooling, occasionally even during the removal of the water.

In order to increase the optical purity, the crystallized and separated salt pair may be washed, appropriately with acetone or methylisobutylketone, and/or, if necessary, recrystallized.

The salt pair produced with high optical purity and high yield is usually separated by using achiral strong acids, particularly mineral acids and preferably hydrochloric acid. The separation results in the optically active carnitine nitrile salt of the achiral acid and the applied optically active thiazolidine-4-carbonic acid being separated.

The process according to the invention affords a special process-engineering advantage in that the separated acids according to formula (II) do not enter into any irreversible side reactions and are slightly water soluble. This means that they can be recovered in a simple manner with only a minor extraction and distillation effort with yields exceeding 95%. The process for racemate resolution is furthermore characterized by a high space-time yield.

Due to the high optical and excellent chemical purity of the crystallizing DL- or LD-salt pairs, the use of the L-acids for the crystallization and separation of the "false" LD-salt pair represents an advantageous process. The isolation of the desired L-carnitine nitrile chloride takes place according to the above-described separation of the mother liquor with hydrochloric acid through crystallization from an alcohol/water mixture.

The conversion of an L-carnitine nitrile chloride into L-carnitine proceeds in a known manner by heating the chloride with concentrated hydrochloric acid and reacting the produced L-carnitine chloride with a cation exchanger.

EXAMPLES

The invention will be further understood with reference to the following illustrative examples.

EXAMPLE 1

178.7 g (1.0 mol) D,L-carnitine nitrile chloride was dissolved in 1 liter of water and pumped over an ion exchanger column (diameter 55 mm, length 90 cm) filled with a highly basic resin (Amberlite IRA-410) in the OH$^-$ form. The obtained D,L-carnitine nitrile hydroxide solution was neutralized with 217.3 g (1.0 mol) D-3-formyl-2,2,5,5-tetramethyl thiazolidine-4-carbonic acid during stirring. The water was distilled off under reduced pressure. The still warm residue was mixed up with 200 ml methylisobutylketone (MIBK) and distilled over a water separator for residual dehydration. When no more water distilled over, the oil-crystalline paste was mixed with 400 ml acetone and vigorously stirred 30 minutes during reflux. The suspension was left to cool to 20° C., the precipitate was suctioned off and acetone was used for washing. The acetonemoist salt pair was suspended in 300 ml acetone for subsequent purification. 30 minutes at boiling temperature and subsequently stirred for 2 more hours at 20° C. The precipitate was suctioned off, washed with acetone and dried. There was obtained 128.7 g (71.5%) colorless salt pair from the reacted D-thiazolidine-4-carbonic acid and the L-carnitine nitrile hydroxide (DL-salt pair) with $(\alpha)_D^{20} = +31.7°$ (c=$\lambda$, water) mp: 158°-160° C.

Elementary analysis calculated for $C_{16}H_{29}N_3O_4S$: C 53.46, H 8.13, N 11.69, S 8.92. found: C 53.20, H 8.40, N 11.51, S 8.63.

EXAMPLE 2

For the salt pair separation, the salt pair from Example 1 was dissolved in 250 ml water during stirring. The solution was cooled to 10° C. and, while maintaining this temperature, a pH value of 2 was set by adding 34.8 g concentrated hydrochloric acid (0.353 mol) dropwise. Having finished adding, stirring was continued for ca. 30 minutes. The obtained precipitate was suctioned off, rewashed with cold water and dried. There was obtained 72.6 g (93.3%) colorless D-(+)-3-formyl-2,2,5,5-tetramethyl thiazolidine-4-carbonic acid with $(\alpha)_D^{20} = 52.0°$ (c=1, ethanol).

The aqueous filtrate was extracted 3 times, each with 40 ml MIBK, and the combined extracts rotated until dryness and then dried to obtain: 2.7 g (3.5%) D-separation acid (recovery=96.8%).

The extracted aqueous filtrate was rotated to dryness, digested with acetone, suctioned off and dried to yield: 62.7 g (98%) colorless L-carnitine nitrile chloride with $(\alpha)_D^{20} = -25.9°$ (c=1, water).

62.5 g (0.35 mol) of this L-carnitine nitrile was dissolved while stirring in 120 g concentrated hydrochloric acid and heated stepwise from 50° to 80° C. for 6 hours, whereby ammonium chloride separated out. After allowing to stand overnight, the suspension was cooled to 5° C., the precipitate filtered off and rewashed with cold concentrated HCl. The filtrate was freed as much as possible from excessive hydrochloric acid at max. 70° C. in vacuum. L-carnitine chloride remained as an oily solids-containing mixture which was dissolved in ca. 300 ml water for the release of L-carnitine and pumped over an ion-exchange column loaded with 500 ml Amberlite IRA 410/OH$^-$-form. The chloride-free solution so obtained was evaporated in vacuum to dryness. The slightly yellowish residue was stirred with an n-butanol/acetone mixture. The coarse-crystalline precipitate obtained thereby was suctioned off, washed with acetone and dried to obtain: 50.6 g (90%) colorless L-carnitine with $(\alpha)_D^{20} = -31.1°$ (c=1, water).

EXAMPLE 3

A D,L-CAN-hydroxide solution produced in the same way as in Example 1 from 178.7 g (1 mol) D,L-carnitine nitrile chloride was set to pH=6.8 with 215.8 g (0.99 mol) L-3-formyl-2,2,5,5-tetramethyl thiazolidine-4-carbonic acid and concentrated in the rotary evaporator. The still warm residue was mixed with 200 ml MIBK and distilled under reduced pressure over a water separator for dehydration.

An oily-crystalline paste is obtained which was vigorously stirred at boiling temperature for 0.5 hours with 400 ml acetone. After further stirring for 2 hours at 20° C., the precipitate was filtered off and washed with acetone. The acetone-moist salt pair was subsequently suspended in 250 ml acetone, heated to boiling temperature for 30 minutes, and finally stirred 2 hours at 20° C. The precipitate was suctioned off, washed with acetone and dried to yield: 129.2 g (71.8%) colorless (LD)-salt pair, $(\alpha)_D^{20} = -35.2°$ C. (c=1, water). mp: 159°-161° C.

Elementary analysis computed for $C_{16}H_{29}N_3O_4S$: C 53.46, H 8.13, N 11.69. found: C 53.21, H 8.34, N 11.75.

EXAMPLE 4

126 g (0.35 mol) (LD)-salt pair from Example 3 was dissolved in 200 ml water and set to pH - 2.0 during stirring at 10°-15° C. with 34.8 g (0.353 mol) 37% hydrochloric acid. The obtained L-3-formyl-2,2,5,5-tetramethylthiazolidine-4-carbonic acid was suctioned off, washed with water and dried. The product was 71.0 g (93.4%) colorless L-separation acid with $(\alpha)_D^{20} = -52.0°$ (c=1, ethanol).

The aqueous filtrate was extracted 3 times, each with 40 ml MIBK, the combined extracts rotated until dryness and then dried: 2.7 g (3.5%) separation acid (recovery=96.9%).

The extracted aqueous filtrate was rotated until dryness, digested with acetone and then dried: 61.2 g (97.9%) colorless D-carnitine nitrile chloride with $(\alpha)_D^{20} = +25.8°$ (c=1, water).

EXAMPLE 5

The mother liquor of the racemate resolution and of the (LD)-salt pair aftertreatment in Example 3 were combined and distilled off, first under normal pressure, then toward the end of the distillation under reduced acetone pressure. After cooling to 20° C., the yellow solution was mixed with 450 ml water. The yellow-colored MIBK phase was separated from the 2-phase mixture. The aqueous phase was stripped on in partial vacuum in order to remove the remaining MIBK. Subsequently, the aqueous mother liquor was cooled off and the solution was set to pH=2.0 at 10°-15° C. inside temperature while stirring and cooling with 62 g (0.628 mol) concentrated hydrochloric acid.

Thereupon, stirring was performed for an additional 30 minutes at 10° C. and the obtained L-separation acid was suctioned off, washed with water and dried. There was obtained 131.0 g (94.1%) colorless L-3-formyl-2,2,5,5-tetramethyl thiazolidine-4-carbonic acid with $(\alpha)_D^{20} = 51.7°$ (c=1, ethanol).

The filtrate was extracted 3 times with 50 ml MIBK and the combined organic phases evaporated until dryness: 3.4 g (2.4%) L-separation acid (recovery=96.5%).

The aqueous solution was evaporated to a crystal paste that was still well stirrable, mixed with 150 ml n-butanol and distilled until complete dehydration under reduced pressure over a water separator. The obtained suspension was mixed at boiling temperature with 300 ml methanol with 10% by volume of water. After letting cool to room temperature, it was restirred 1 hour. The obtained precipitate was suctioned off, washed with methanol and dried: 62.8 g (35% relative to the applied D,L-compound) L-carnitine nitrile chloride with $(\alpha)_D^{20} = -25.9°$ (c=1, water).

60.8 g (0.34 mol) of the L-carnitine nitrile chloride obtained in this manner was saponified with 108 g 37% hydrochloric acid as in Example 2 and processed to obtain: 50.4 g (91.9%) L-carnitine with $(\alpha)_D^{20} = -30.8°$ (c=1, water). HPLC>99%.

EXAMPLE 6

A D,L-carnitine nitrile hydroxide solution produced in the same way as in Example 1 from a 60.7 g D,L-carnitine nitrile chloride was set to pH=6.0 with 78.5 g (0.34 mol) L-(−)-3-formyl-2,2-pentamethylene thiazolidine-4-carbonic acid and concentrated in the rotary evaporator. The residue was stirred with 610 ml n-butanol and distilled over a water separator for dehydration. After cooling to 20° C., it was stirred an additional 2 hours, whereupon the LD-salt pair was filtered off from the L-thiazolidine-4-carbonic acid and the D-carnitine nitrile hydroxide, and dried. The yield was 38.6 g (61.1%).

33.4 g of the LD-salt pair was recrystallized from 130 ml n-butanol/acetone and the 26.3 g, obtained after drying as described in Example 2, was separated. 16.2 g (99%) L-(−)-3-formyl-2,2-pentamethylene thiazolidine-4-carbonic acid is recovered without extraction from the aqueous mother liquor. The aqueous filtrate was concentrated by evaporation and dried. The yield was 12.3 g (97.2%) D-carnitine nitrile chloride (46.7% of theory) with $(\alpha)_D^{20} = +22.1°$ (c=1, water).

The mother liquors of the racemate resolution as well as of the salt pair recrystallization were combined and evaporated. The remaining solid substance was dissolved in 280 ml water and reacted with 50 g concentrated hydrochloric acid at 0° C. The precipitated L-thiazolidine carbonic acid obtained was suctioned off and dried: 56.3 g (96.2%). The aqueous filtrate was evaporated and the crystalline residue consisting of aqueous methanol recrystallized to obtain: 27.34 g (90%) L-carnitine nitrile chloride with $(\alpha)_D^{20} = -10.9°$ (c =1, water). An additional recrystallization of 26.5 g provided 11.88 g (40.4% of theory) L-carnitine nitrile chloride with $(\alpha)_D^{20} = -22.9°$ (c=1, water).

EXAMPLE 7

As described in Example 1, 55.4 kg D.L-carnitine nitrile chloride (content 96.8%) was dissolved in 300 liter water and converted into the hydroxide form in the ion exchanger (400 liter Amberlite IRA-416, OH−-form). After neutralization with 68.3 kg D-3-formyl-2,2,5,5-tetramethyl thiazolidine-4-carbonic acid, water was distilled off under reduced pressure. Residual amounts of water were removed after addition of 60 liters MIBK by means of azeotrope distillation in the water separator. Thereupon 120 liters acetone was added to the DL-salt pair crystallization and heated for 0.5 hours. After cooling to room temperature, the DL-salt pair was centrifuged off, washed in the centrifuge 3 times, each with 30 liters acetone, and dried. There was obtained 40.6 kg (75.3% of theory). DL-salt pair, which was dissolved in 75 liters water for separation, as described in Example 2, and mixed with 97 liters concentrated hydrochloric acid at 10° C. The precipitated D-thiazolidine carbonic acid obtained was centrifuged off, washed with water and returned moist (30.1 kg) in the separation process (recovery portion 94%). The aqueous filtrate was extracted twice with 15 liters MIBK. Of the combined extracts, separation reagent (2.5%) was recovered.

The aqueous L-carnitine nitrile chloride-containing mother liquor (evaporation and drying of a sample yielded $(\alpha)_D^{20} = -25.9°$; c=1, H₂O) was concentrated, mixed with 32.9 liters concentrated hydrochloric acid and saponified to L-carnitine chloride as described in Example 2. It was subsequently reacted to betaine in the ion exchanger (Amberlite IRA-416). 15.9 kg colorless L-carnitine (32% relative to D,L-carnitine nitrile chloride) was isolated with $(\alpha)_D^{20} = -30.7°$ and an HPLC concentration>99%.

EXAMPLE 8

As described in Example 1, 56.3 kg D.L-carnitine nitrile chloride (concentration 95.0%) was dissolved in 300 liters water and converted into hydroxide form in the ion exchanger (Amberlite IRA-416, OH−-form). After neutralization with 68.0 kg L-3-formyl-2,2,5,5-tetramethyl thiazolidine-4-carbonic acid, distillation under reduced pressure took place. Remaining amounts of water were removed after addition of 60 liters MIBK by way of azeotrope distillation in the water separator. Subsequently, 120 liters acetone was added to the LD-salt-pair crystallization and heated for 0.5 hours. After cooling to room temperature, the LD-salt pair was centrifuged off, washed on the centrifuge 3 times, each with 30 liters acetone, and dried. There was obtained 37.0 kg (69.4% of theory). LD-salt pair, which was dissolved in 75 liters water for separation as described in Example 4 and mixed with 8.2 concentrated hydrochloric acid at 10° C. The obtained L-thiazolidine carbonic acid was centrifuged off, washed with water and returned moist (25.9 kg) in the separation process.

As described in Example 5, the mother liquors of the racemate resolution as well as the acetone washing were combined and the acetone was separated by way of distillation. Thereupon, 130 liters water was added and the phases separated. The aqueous phase was stripped following A-carbon treatment, cooled to 10° C. and set to pH 2 with 19.5 liters concentrated hydrochloric acid. The obtained L-thiazolidine carbonic acid was centrifuged off, washed with water and returned moist (59.5 kg) in the separation process.

The mother liquor was evaporated as much as possible after extracting 3 times with MIBK (recovery of remaining separation acid), mixed with 90 liters methanol and heated 30 minutes during reflux. After letting cool to room temperature, 27.7 kg moist L-carnitine nitrile chloride with $(\alpha)_D^{20} = -22.9°$ ) was isolated, heated 30 minutes for additional purification in 40 liters methanol.

After filtration, washing with 20 liters methanol and drying, 18.2 kg (34% relative to D,L-carnitine nitrile chloride) was obtained with $(\alpha)_D^{20} = -25.6°$ (c=1, water); HPLC concentration >99.9%.

The mother liquors of the L-carnitine nitrile chloride isolation were combined and evaporated until formation of crystals. After cooling to room temperature, 10.8 kg D,L-carnitine nitrile chloride $(\alpha)_D^{20} = -3.0°$) was isolated and returned to the separation process.

13.5 kg L-carnitine nitrile chloride was dissolved in 22 liters concentrated hydrochloric acid and hydrolyzed to L-carnitine chloride, as described in Example 2. It was subsequently reacted to betaine in the highly basic ion exchanger (Amberlite IRA-416). After appropriate reprocessing, 11.1 kg colorless L-carnitine with $(\alpha)_D^{20} = -30.8°$ and an HPLC concentration of 99.7% was isolated.

In the compounds of the invention, the Ac (acyl) group can contain 1 to 7 carbon atoms.

Further variations and modifications of the foregoing will be apparent to those skilled in the art and are intended to be encompassed by the claims appended hereto.

German priority application P 40 15 537.0-44 is relied on and incorporated herein by reference.

We claim:

1. An optical active of the formula (I):

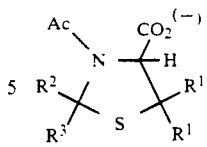 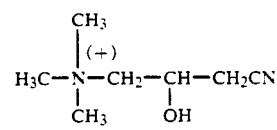

where
R¹ represents hydrogen or methyl;
R² and R³, which may be identical of different, represent hydrogen, alkyl with 1 to 8 C-atoms, alkenyl with 2 to 8 C-atoms, C₅ or C₆ cycloalkyl, or R² and R³ taken together are alkylene with 4 to 11 C-atoms; and Ac represents an acyl group selected from the group consisting of benzoyl, tosyl, nitrophenyl, sulfonyl, acetyl and formyl.

2. The optical salt according to claim 1 where R² and R³ are identical.

3. The optical salt according to claim 1 wherein R² and R³ are identical and are methyl or ethyl.

4. The optical salt according to claim 1 where R² and R³ are taken together as pentamethylene.

5. The optical salt according to claim 1 where the Ac is formyl.

6. The optical salt according to claim 1 which is formed from D-(+)-3-formyl-2,2,5,5-tetramethyl thiazolidine-4-carboxylate and L-(−)-3-cyano-2-hydroxypropyl trimethylammonium.

7. The optical salt according to claim 1 which is formed from L-(−)-3-formyl-2,2,5,5-tetramethyl thiazolidine-4-carboxylate and D-(+)-3-cyano-2-hydroxypropyl trimethylammonium.

* * * * *